US005644028A

United States Patent [19]
Mimoto et al.

[11] Patent Number: 5,644,028
[45] Date of Patent: Jul. 1, 1997

[54] PROCESS FOR PRODUCING PEPTIDE DERIVATIVES AND SALTS THEREFOR

[75] Inventors: Tsutomu Mimoto; Sumitsugu Kisanuki; Osamu Takahashi, all of Tokyo; Yoshiaki Kiso, Ibaraki, all of Japan

[73] Assignee: Japan Energy Corporation, Japan

[21] Appl. No.: 364,707

[22] Filed: Dec. 28, 1994

Related U.S. Application Data

[63] Continuation-in-part of Ser. No. 60,535, May 13, 1993, abandoned.

[30] Foreign Application Priority Data

| May 13, 1992 | [JP] | Japan | 4-192653 |
| May 13, 1992 | [JP] | Japan | 4-192654 |
| May 25, 1992 | [JP] | Japan | 4-157459 |
| Oct. 30, 1992 | [JP] | Japan | 4-315640 |
| Nov. 9, 1992 | [JP] | Japan | 4-323599 |

[51] Int. Cl.$^6$ .................. C07K 1/02; C07K 1/08; C07K 1/10; C07K 5/083
[52] U.S. Cl. .................. 530/331; 530/332; 530/337; 530/338; 530/340; 530/341
[58] Field of Search .................. 514/18; 530/331, 530/332, 333, 335, 337, 338, 340, 341

[56] References Cited

U.S. PATENT DOCUMENTS

| 4,543,349 | 9/1985 | Callahan et al. | 530/329 |
| 5,037,956 | 8/1991 | Wideman et al. | 524/270 |
| 5,191,065 | 3/1993 | Flemming et al. | 530/331 |

FOREIGN PATENT DOCUMENTS

| 490667 | 6/1992 | European Pat. Off. | |
| 0 498 680 A1 | 8/1992 | European Pat. Off. | C07D 207/16 |

OTHER PUBLICATIONS

Chem. Pharm. Bull., vol. 40, No. 8, issued Aug. 1992, Mimoto et al, "Kynostatin (KNI)–227 and –272 . . . ", pp. 2251–2253.
J. Chem. Soc., Issued 1960, Frankel et al., "Syntheses of Poly–S–alkyl–L–cysteines", pp. 1390–1393.
Helvetica Chimica Acta, vol. XXIX, Fasciculus VII, issued 1946.
Neher et al, "Synthese Penicillin . . . ", pp. 1874–1882.
J. Am. Chem. Soc., vol. 59, issued 1937, Ratner et al. "The Action of Formaldehyde upon Cysteine", pp. 200–206.
Greene, "Protective Groups in Organic Synthesis", published Jun. 1981, John Wiley & Sons (NY), pp. 195–196, 232–233.
J. Med. Chem., vol. 20, No. 4, issued 1977, Nishizawa et al, "Synthesis and Structure–Activity Relationships . . . ", pp. 510–515.
J. Med. Chem. vol. 19, No. 7, issued 1976, Rosamond et al., "Synthesis and Some Pharmacological Properties . . . ", pp. 873–876.

T. Mimoto et al., 117:8449h "Design and synthesis of HIV protease inhibitors containing a hydroxmethylcarbonyl isostere as a transition–state mimic", *Chemical Abstracts*, 117(1):2(1992).

Primary Examiner—Jeffrey E. Russel
Attorney, Agent, or Firm—Testa, Hurwitz & Thibeault, LLP

[57] ABSTRACT

A process for producing peptide derivatives of formula (1) or salts thereof:

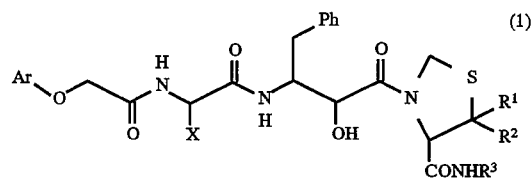

which comprises condensation of peptide derivative of formula (2):

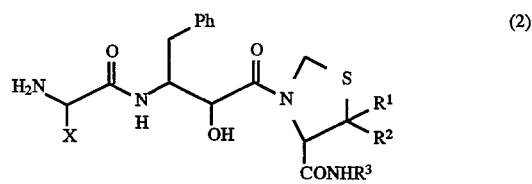

with carboxylic acid of formula (3):

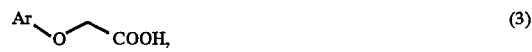

or condensation of a peptide derivative of formula (4):

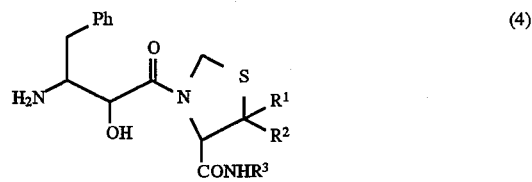

with a protected amino acid of formula (5'):

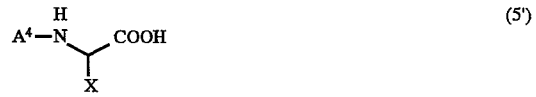

wherein $R^1$ and $R^2$ are a lower alkyl group or hydrogen atom, $R^3$ is a lower alkyl group, X is a methylthiomethyl, methanesulfonylmethyl, carbamoylmethyl, or a lower alkyl group, Ar is an aryl or heteroaryl group, and $A^4$ is Ar—O—$CH_2$—CO. The peptide derivatives and salts thereof are useful as the human immunodeficiency virus (HIV) protease inhibitors.

7 Claims, No Drawings

PROCESS FOR PRODUCING PEPTIDE DERIVATIVES AND SALTS THEREFOR

This is a continuation-in-part of application Ser. No. 08/060,535 filed on May 13, 1993 now abandoned.

BACKGROUND OF THE INVENTION

1. Field of the Invention

The present invention relates to a process for producing peptide derivatives and salts thereof which are useful as human immunodeficiency virus (HIV) protease inhibitors.

2. Description of the Related Art

Heretofore, various efforts have been performed for the therapy of acquired immunodeficieney syndrome (AIDS) and prevention of infection of HIV by inhibiting the HIV protease. The present inventors have proposed peptide derivatives and salts thereof which inhibit the HIV protease [European Patent No. 490667 (1992)]. The methods for producing said peptide derivatives and salts thereof, however, have been expensive and/or required toxic reagents, for example, Bop reagent.

SUMMARY OF THE INVENTION

It is an object of the present invention to provide a convenient process for producing peptide derivatives and salts thereof which inhibit HIV protease without using expensive and/or toxic reagents.

The object of the present invention has been attained by the following process for producing peptide derivatives represented by the following formula (1) and salts thereof:

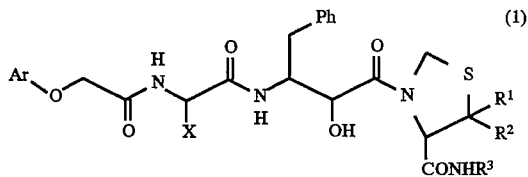

(wherein $R^1$ and $R^2$ represent a lower alkyl group or hydrogen atom, $R^3$ represents a lower alkyl group, X represents methylthiomethyl, methanesulfonylmethyl, carbamoylmethyl, or a lower alkyl group, Ar represents an aryl group or a heteroaryl group); the process comprises a condensation reaction (step A) of a peptide derivative represented by the formula (2):

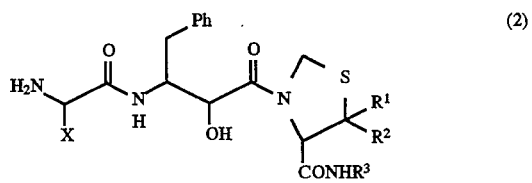

(wherein $R^1$, $R^2$, $R^3$, and X are as defined above) with a carboxylic acid represented by the following formula (3):

(wherein Ar is as defined above), or a condensation reaction (step B') of a peptide derivative represented by the following formula (4):

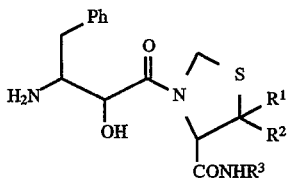

(wherein $R^1$, $R^2$, and $R^3$ are as defined above) with a protected amino acid represented by the following formula (5'):

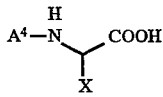

(wherein $A^4$ represents an acyl group derived from the carboxylic acid represented by the formula (3), X is as defined above) which gives a peptide derivative represented by the formula (1).

The object of the present invention also has been attained by the following process for producing peptide derivatives represented by the following formula (1) and salts thereof:

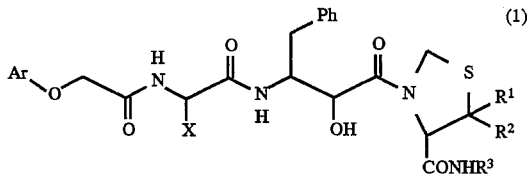

(wherein $R^1$, $R^2$, $R^3$, X, and Ar are defined above), which process comprises a condensation reaction (step C) of a protected amino acid represented by the following formula (6):

(wherein $R^1$ and $R^2$ represents a lower alkyl group or hydrogen atom, $A^1$ represents an amino protective group) with an amine represented by the following formula (7):

(wherein $R^3$ represents a lower alkyl group) which gives a protected amino amide represented by the following formula (8):

(wherein $A^1$, $R^1$, $R^2$, and $R^3$ are as defined above), a deprotection reaction (step D) of said protected amino amide which gives an amino amide represented by the following formula (9):

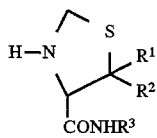

(wherein R¹, R², and R³ are as defined above), a condensation reaction (step E) of said amino amide with a protected amino acid represented by the following formula (10):

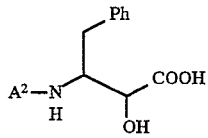

(wherein A² represents an amino protective group) which gives a protected peptide represented by the following formula (11):

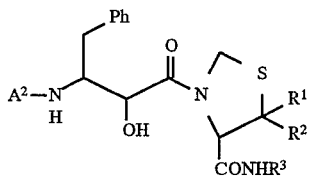

(wherein A², R¹, R², and R³ are as defined above), a deprotection reaction (step F) of said protected peptide which gives a peptide represented by the following formula (4)

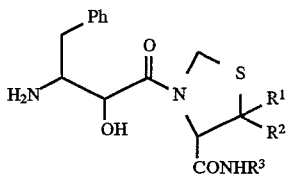

(wherein R¹, R², and R³ are as defined above), a condensation reaction (step B) of said peptide with a protected amino acid represented by the following formula (5):

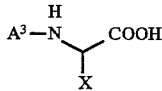

(wherein A³ represents an amino protective group, X represents methylthiomethyl, methanesulfonylmethyl, carbamoylmethyl, or a lower alkyl group) which gives a protected peptide represented by the following formula (12):

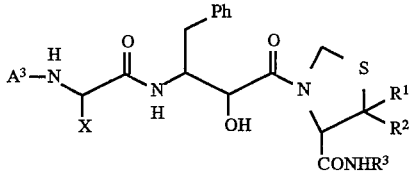

(wherein A³, R¹, R², R³, and X are as defined above), a deprotection reaction (step G) of said protected peptide which gives a peptide represented by the following formula (2):

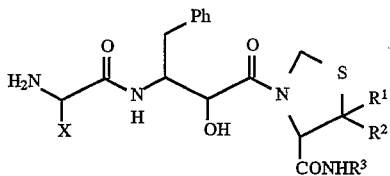

(wherein R¹, R², R³, and X are as defined above), and a condensation reaction (step A) of said peptide with a carboxylic acid represented by the following formula (3):

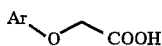

(wherein Ar represents an aryl group or a heteroaryl group), or a condensation reaction (step B') of a peptide derivative represented by the following formula (4):

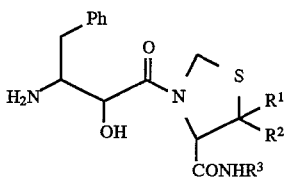

(wherein R¹, R², and R³ are as defined above) with a protected amino acid represented by the following formula (5'):

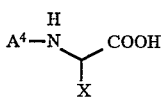

(wherein A⁴ and X are as defined above) which gives a peptide derivative represented by the formula (1).

Among the starting materials of the above process, a compound represented by formula (6) wherein A¹ represents tert-butoxycarbonyl may be produced by cyclization of a compound represented by the following formula (13):

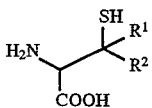

(wherein R¹ and R² are as defined above), or the salt thereof using formaldehyde and a subsequent one-pot aminoprotection using di-tert-butyl dicarbonate (step I).

In addition, a compound represented by the formula (5) wherein X represents methylthiomethyl and A³ represents tert-butoxycarbonyl may be produced by methylation of cysteine and a subsequent one-pot amino-protection using di-tert-butyl dicarbonate (step II).

DETAILED DESCRIPTION OF THE INVENTION

As a protective group of the present invention represented by A¹, A², and A³, amino protective groups which are generally used in peptide synthesis, for example p-methoxybenzyloxycarbonyl or tert-butoxycarbonyl, may be used. As a lower alkyl group represented by R¹, R², R³, and X, there may be mentioned methyl, ethyl, propyl, isopropyl, n-butyl, sec-butyl, tert-butyl, and amyl. As an aryl group represented by Ar, there may be mentioned phenyl, 1-naphthyl, 5-isoquinolyl, and 3-pyridyl.

The amino deprotection of the present invention may be carried out by acids, and the peptide bond formation may be carried out by a mixed-anhydride method, a carbodiimide-additive method, or an active-ester method.

As the amino acid corresponding to the compound represented by the formula (6), there may be mentioned 1,3-thiazolidine-4-carboxylic acid [H—Thz—OH] and 5,5-dimethyl-1,3-thiazolidine-4-carboxylic acid [H—Dtc—OH]. Any amino protective group which is removed under acidic condition may be used for the group represented by $A^1$ in the formula (6), however, tert-butoxycarbonyl is preferred. Any lower alkyl group may be used for the group represented by $R^3$ in the formula (7) from the synthetic point of view, however, tert-butyl is preferred for HIV protease inhibitory activity.

As the condensation method of the step C, a mixed-anhydride method and an active-ester method are preferred. In the mixed-anhydride method, an acyl chloride (normally 1.0–1.5 eq) is added into a solution of the compound represented by the formula (6) in the presence of an organic amine (normally 1.0–1.5 eq) to form the mixed anhydride. As said acyl chloride, for example, isobutyl chloroformate, isopropyl chloroformate, and pivaloyl chloride may be used. As said organic amine, for example, triethylamine and N-methylmorpholine may be used. As the reaction solvent, for example, tetrahydrofuran [THF], dimethoxyethane, acetonitrile, ethyl acetate, N,N-dimethylformamide [DMF], and the mixed solvent thereof may be used. The reaction temperature between −20° and −10° C. is preferred.

In the active-ester method, a carbodiimide (normally 1.0–1.5 eq) is added into a solution of the compound represented by the formula (6) in the presence of a hydroxyl compound such as N-hydroxybenzotriazole [HOBt] or N-hydroxysuccinimide [HOSu] (normally 1.0–1.5 eq) to form the active ester. Said reaction may be carried out in the presence of an organic amine such as pyridine. As said carbodiimide, for example, N,N'-dicyclohexylcarbodiimide [DCC] and 1-ethyl-3-(3-N,N-dimethylaminopropyl) carbodiimide [EDC] may be used, and the economically cheaper DCC is more preferred. As the reaction solvent, for example, THF, dioxane, dichloromethane, chloroform, acetonitrile, DMF, and the mixed solvent thereof may be used. The reaction temperature between 0° and 30° C. is preferred.

The mixed anhydride or the active ester obtained by the above operation is reacted with the amine represented by the formula (7). The reaction mixture of said mixed anhydride or the active ester may be used without isolation. Normally 1–5 equivalent of said amine may be used, and excess amount of said amine, especially more than 2 equivalent, may preferably be used to raise the yield. The reaction temperature between −20° and 30° C. is preferred and that between −10° and 15° C. is more preferred. The compound represented by the formula (8) is obtained by the usual work-up after completion of the reaction.

The deprotection of the step D is easily performed under an acidic condition. As the acid, for example, hydrogen chloride, hydrogen bromide, trifluoroacetic acid, methanesulfonic acid, and toluenesulfonic acid (normally 2–20 eq) may be used. As the reaction solvent, for example, methanol, dioxane, dichloromethane, acetic acid, formic acid, acetonitrile, ethyl acetate, and the mixed solvent thereof may be used. Said acid, amount of the acid, and said solvent may be chosen according to the protective group represented by $A^1$. The compound represented by the formula (9) is produced as the corresponding ammonium-type salt, and said salt may be neutralized with a tert-amine such as triethylamine or N-methylmorpholine in the solvent of the subsequent step D. The compound represented by the formula (9) may also be used after isolation by alkaline work-up.

As the condensation method of the step E, a carbodiimide-additive method is preferred. To a solution or suspension of the compound represented by the formula (9), the compound represented by the formula (10) (normally 0.8–1.2 eq, more preferably 0.9–1.1 eq) and an additive of the carbodiimide-additive method (normally 0.2–1.2 eq, more preferably 0.8–1.1 eq) in a reaction solvent, a carbodiimide (normally 1.0–1.5 eq, more preferably 1.0–1.2 eq) is added and reacts. Any amino protective group which is removed under acidic conditions may be used for the group represented by $A^2$ in the formula (10), however, tert-butoxycarbonyl is preferred. As said additive, a hydroxyl compound such as HOBt, HOSu, N-hydroxy-5-norbornene-2,3-dicarboximide [HONb], or 3-hydroxy-4-oxo-3,4-dihydro-1,2,3-benzotriazine may be used, however, HOBt and HOSu are more preferred. As the reaction solvent, for example, THF, dioxane, acetonitrile, chloroform, dichloromethane, DMF, and the mixed solvent thereof may be used. As said carbodiimide, for example, DCC and EDC may be used, and the economically cheaper DCC is more preferred. The reaction temperature between 0° and 30° C. is preferred. The compound represented by the formula (11) is obtained by the usual work-up after completion of the reaction. Purification, for example, by silica-gel column chromatography may be performed.

The deprotection of the step F is easily performed under an acidic condition similarly to that in the step D. As the acid, for example, hydrogen chloride, hydrogen bromide, trifluoroacetic acid, methanesulfonic acid, and toluenesulfonic acid (normally 2–20 eq) may be used. As the reaction solvent, for example, methanol, dioxane, dichloromethane, acetic acid, formic add, acetonitrile, ethyl acetate, and the mixed solvent thereof may be used. Said acid, amount of the acid, and said solvent may be chosen according to the protective group represented by $A^2$. The compound represented by the formula (4) is produced as the corresponding ammonium-type salt, and said salt may be neutralized with a tert-amine such as triethylamine or N-methylmorpholine in the solvent of the subsequent Step B or B' to use. The compound represented by the formula (4) may also be used after isolation by alkaline work-up.

As the condensation method of the step B, a carbodiimide-additive method or an active-ester method is preferred. In the carbodiimide-additive method, a carbodiimide (normally 1.0–1.5 eq, more preferably 1.0–1.2 eq) is added to a solution or suspension of the compound represented by the formula (4), the compound represented by the formula (5) (normally 1.0–1.2 eq) and an additive of the carbodiimide-additive method (normally 0.2–1.2 eq, more preferably 0.8–1.1 eq) in a reaction solvent to react. As the amino acid corresponding to the compound represented by the formula (5), there may be mentioned methylthioalanine [H—Mta—OH], methanesulfonylalanine [H—Msa—OH], asparagine [H—Asn—OH], valine [H—Val—OH], isoleucine [H—Ile—OH], and alanine [H—Ala—OH]. Any amino protective group which is removed under acidic condition may be used for the group represented by $A^3$ in the formula (5), however, tert-butoxycarbonyl is preferred. As said additive, a hydroxyl compound such as HOBt, HOSu, HONb, or p-nitrophenol [HONp] may be used. As the reaction solvent, for example, THF, dioxane, acetonitrile, chloroform, dichloromethane, DMF, and the mixed solvent thereof may be used. As said carbodiimide, for example, DCC and EDC may be used, and the economically cheaper DCC is more preferred. A reaction temperature between 0° and 30° C. is preferred. The compound represented by the formula (12) is obtained by the usual work-up after completion of the reaction. Purification, for example, by silica-gel column chromatography or recrystallization may be performed.

In the active-ester method, a carbodiimide (normally 1.0–1.5 eq) is added into a solution of the compound represented by the formula (5) in the presence of a hydroxyl compound such as HOBt, HOSu, HONb, or HONp (normally 1.0–1.5 eq) to form the active ester. Said reaction may be carried out in the presence of an organic amine such as pyridine. Said active ester is obtained by the usual work-up after the completion of the reaction. As said carbodiimide, for example, DCC and EDC may be used, and the economically cheaper DCC is more preferred. As the reaction solvent, for example, THF, dioxane, dichloromethane, chloroform, acetonitrile, DMF, and the mixed solvent thereof may be used. A reaction temperature between 0° and 30° C. is preferred.

Said active ester is reacted with the compound represented by the formula (4) in the presence of amine such as triethylamine or N-methylmorpholine (normally 1.0–1.5 eq). The presence of a hydroxyl compound such as HOBt or HOSu (normally 0.5–1.5 eq) is more preferred. As the reaction solvent, for example, THF, dioxane, dichloromethane, chloroform, acetonitrile, DMF, dimethylsulfoxide, and the mixed solvent thereof may be used. A reaction temperature between 0° and 30° C. is preferred. The compound represented by the formula (12) is obtained by the usual work-up after the completion of the reaction. Purification, for example, by silica-gel column chromatography or recrystallization may be performed.

The deprotection of the step G is easily performed under an acidic condition similarly to that in the step D. As the acid, for example, hydrogen chloride, hydrogen bromide, trifluoroacetic acid, methanesulfonic acid, and toluenesulfonic acid (normally 2–20 eq) may be used. As the reaction solvent, for example, methanol, dioxane, dichloromethane, acetic acid, formic acid, acetonitrile, ethyl acetate, and the mixed solvent thereof may be used. Said acid, amount of the acid, and said solvent may be chosen according to the protective group represented by $A^3$. The compound represented by the formula (2) is produced as the corresponding ammonium-type salt, and said salt may be neutralized with a tert-amine such as triethylamine or N-methylmorpholine in the solvent of the subsequent step A. The compound represented by the formula (2) may also be used after isolation by alkaline work-up.

As the condensation method of the step A, a carbodiimide-additive method is preferred. To a solution or suspension of the compound represented by the formula (2), the compound represented by the formula (3) (normally 1.0–1.2 eq), an additive of the carbodiimide-additive method (normally 0.2–1.2 eq, more preferably 0.8–1.1 eq) in a reaction solvent, a carbodiimide (normally 1.0–1.5 eq, more preferably 1.0–1.2 eq) is added to react. As said compound represented by the formula (3), there may be mentioned 1-naphthyloxyacetic acid [Noa—OH], 5-isoquinolyloxyacetic acid [Qoa—OH], or 3-Pyridyloxyacetic acid [Pyoa—OH]. As said additive, a hydroxyl compound such as HOBt, HOSu, HONb, or HONp may be used, however, HOBt and HOSu are more preferred. As the reaction solvent, for example, THF, dioxane, acetonitrile, chloroform, dichloromethane, DMF, and the mixed solvent thereof may be used. As said carbodiimide, for example, DCC and EDC may be used, and the economically cheaper DCC is more preferred. The reaction temperature between 0° and 30° C. is preferred. The compound represented by the formula (1) is obtained by the usual work-up after completion of the reaction.

Activation of the carboxylic acid represented by formula (3), which generates an activated ester represented by formula (14):

$$Ar\text{—}O\text{—}CH_2\text{—}COOR^4 \quad (14)$$

(wherein $R^4$ represents a group selected from benzotriazol-1-yl, succinimido, 5-norbornene-2,3-dicarboximido, or nitrophenyl), may also be performed by a reaction with a phosphate ester represented by formula (15):

$$(R^5O)(R^6O)P(=O)(OR^4) \quad (15)$$

(wherein $R^5$ and $R^6$ each represent a hydrocarbon group having 7 or less carbon atoms, and $R^4$ is defined above). As the phosphate ester of formula (15), for example, benzotriazol-1-yl diphenyl phosphate [S. Kim, et al, Bull. Korean Chem. Soc., 1987, Vol. 8, 471] or 5-norbornene-2,3-dicaboximido diphenyl phosphate [Y. Kiso, et al, J. Chem. Soc., Chem. Comm., 1980, 1029] can be used. The phosphate ester of formula (15) may be generated in situ by addition of phosphoryl chloride represented by formula (16):

$$(R^5O)(R^6O)P(=O)Cl \quad (16)$$

(where $R^5$ and $R^6$ are defined above) into a solution of a tertiary amine such as triethylamine and a hydroxyl compound represented by formula (17) (wherein $R^4$ is defined above):

$$HO\text{—}R^4 \quad (17)$$

To the reaction mixture thus obtained, are added the carboxylic acid represented by formula (3), the compound represented by formula (2), and a tertiary amine such as triethylamine successively to react. The similar reaction solvent, temperature, and work-up method as the above mentioned carbodiimide-additive method can be used. Insoluble matter such as N,N'-dicyclohexylurea; which requires filtration for its removal, is not formed. The condensation of compounds of formulae (2) and (3) using the phosphate ester of formula (15), however, requires excess amount of the carboxylic acid of formula (3), e.g. more than 1.5 eq, to obtain satisfactory yield. Formation of the activated ester of formula (14) through ester exchange reaction would be slow because the carboxylic acid of formula (3) is a class of less electrophilic α-oxy carboxylic acids.

Activation of the carboxylic acid represented by formula (3) may also be performed by a reaction with the phosphoryl chloride represented by formula (16) in the presence of the hydroxyl compound represented by formula (17). Into a solution of the carboxylic acid represented by formula (3) (normally 1.0–1.5 eq to the compound of formula (2), more preferably 1.0–1.1 eq), a tertiary amine such as triethylamine (normally 2.0–4.0 eq to the compound of formula (2), more preferably 2.0–2.3 eq), and a hydroxyl compound of formula (17) (normally 1.0–1.5 eq to the compound of formula (2), more preferably 1.0–1.1 eq), is added the phosphoryl chloride represented by formula (16) (normally 1.0–1.5 eq to the compound of formula (2), more preferably 1.0–1.1 eq) to react. As the phosphoryl chloride of formula (16), for example, diethylphosphoryl chloride and diphenylphosphoryl chloride, more preferably diphenylphosphoryl chloride, can be used. As the hydroxy compound of formula (17), 1-hydroxybenzotriazole, N-hydroxysuccinimide, N-hydroxy-5-norbornene-2,3-dicarboximide, or nitrophenol, more preferably, 1-hydroxybenzotriazole or N-hydroxy-5-norbornene-2,3-dicarboximide can be used. To the reaction mixture thus obtained, in which the carboxylic acid represented by formula (3) is rapidly transformed to the corresponding activated ester of formula (14), the compound represented by formula (2) is added to react. The similar reaction solvent, temperature, and work-up method as the above mentioned methods can be used. Insoluble matter such as N,N'-dicyclohexylurea, which requires filtration for its removal, is not formed. Purification, for example, by silica-gel column chromatography or recrystallization may be performed.

In the present invention, the compound represented by the formula (1) may be obtained from the compound represented by the formula (4) by performing condensation step B', instead of carring out steps B, G and A.

As the condensation method of step B', for example, a carbodiimide-additive method is preferred. To a solution or suspension of the compound represented by the formula (4), the compound represented by the formula (5') wherein the amino protective group $A^4$ represents an acyl group derived from the carboxylic acid represented by the formula (3) (normally 1.0–1.2 eq), an additive of the carbodiimide-additive method (normally 0.2–1.2 eq, more preferably 0.8–1.1 eq) in a reaction solvent, and a carbodiimide (normally 1.0–1.5 eq, more preferably 1.0–1.2 eq) is added and reacts. As said compound represented by the formula (5'), there may be mentioned N-(5-isoquinolyloxyacetyl) methylthioalanine, N-(5-isoquinolyloxyacetyl) methanesulfonylalanine, N-(5-isoquinolyloxyacetyl) asparagine, N-(5-isoquinolyloxyacetyl)valine, N-(5-isoquinolyloxyacetyl)isoleucine, N-(5-isoquinolyloxyacetyl)alanine, N-(1-naphthoxyacetyl) methylthioalanine, N-(1-naphthoxyacetyl) methanesulfonylalanine, N-(1-naphthoxyacetyl)asparagine, N-(1-naphthoxyacetyl)valine, N-(1-naphthoxyacetyl) isoleucine, N-(1-naphthoxyacetyl)alanine, N-(3-pyridyloxyacetyl)methylthioalanine, N-(3-pyridyloxyacetyl)methanesulfonylalanine, N-(3-pyridyloxyacetyl)asparagine, N-(3-pyridyloxyacetyl)valine, N-(3-pyridyloxyacetyl)isoleucine, N-(3-pyridyloxyacetyl) alanine. As said additive, a hydroxyl compound such as HOBt, HOSu, HONb, or HONp may be used. As the reaction solvent, for example, THF, dioxane, acetonitrile, chloroform, dichloromethane, DMF, and the mixed solvent thereof may be used. As said carbodiimide, for example, DCC and EDC may be used, and the economically cheaper DCC is more preferred. The reaction temperature between 0° and 30° C. is preferred. The compound represented by the formula (1) is obtained by the usual work-up after completion of the reaction. Purification, for example, by silica-gel column chromatography or recrystallization may be performed.

The compound represented by the formula (1) may be purified by crystallization of the corresponding acid-addition salt when Ar is a basic heteroaryl group. The compound represented by the formula (1) is mixed with a protic acid in a solvent and the salt is crystallized upon standing or cooling. Recrystallization and/or desalting by alkaline work-up may also be performed. As said protic acid, there may be mentioned hydrogen chloride, acetic acid, propionic acid, butyric acid, valeric acid, pivalic acid, succinic acid, maleic acid, fumaric acid, malonic acid, glutaric acid, benzoic acid, salicylic acid, cinnamic acid, tartaric acid, citric acid, methanesulfonic acid, or toluenesulfonic acid. As said solvent, for example, ethanol, propanol, isopropanol, acetone, ethyl acetate, and the mixed solvent thereof may be used.

In the process of the present invention, the compound represented by the formula (1) may be stereospecifically obtained with little epimerization when optically active compounds represented by the formula (6), (10), (5) and (5') are used as the starting materials. Any stereo-isomer is used as said starting material, however, the preferred configuration for the HIV protease inhibitory activity is as follows: R (L) for the compound represented by the formula (6); (2S,3S) for the compound represented by the formula (10); R (L) for methylthioalanine and methanesulfonylalanine derivatives among the compound represented by the formula (5) and (5'); S (L) for asparagine, valine, isoleucine, and alanine derivatives among the compound represented by the formula (5) and (5').

Among said starting materials, the compound represented by the formula (6) wherein $A^1$ represents tert-butoxycarbonyl may be produced by the step I, and the compound represented by the formula (5) wherein X represents methylthiomethyl and $A^3$ represents tert-butoxycarbonyl may be produced by step II.

In the step I, formaldehyde (at least 1.0 eq, preferably 1.2–2.0 eq) is added to an aqueous solution of the compound represented by the formula (13) or salt thereof to cyclize. As the compound represented by the formula (13), for example, cysteine or penicillamine may be used. Formalin may preferably be used as the formaldehyde source. The reaction temperature between −10° and 50° C. is preferred and that between 0° and 30° C. is more preferred. The completion of the cyclization reaction may be detected, for example, by TLC.

To the reaction mixture obtained above, di-tert-butyl dicarbonate (normally 1.0–1.5 eq) is added to react. The reaction may preferably be carried out under neutral or slight basic condition by addition of a base such as triethylamine, N-methylmorpholine, sodium hydroxide, or potassium hydroxide. The presence of a polar organic solvent such as THF or dioxane is also preferred. The reaction temperature between −10° and 50° C. is preferred and that between 0° and 30° C. is more preferred.

Acidification of the above reaction mixture gives the compound represented by the formula (6) wherein $A^1$ represents tert-butoxycarbonyl. As the acid for said acidification, a water soluble organic acid such as citric acid or mineral acid such as hydrochloric acid may be used and hydrochloric acid is cheap and more preferable. Before the acidification, the organic solvent used may preferably be distilled off and the resultant aqueous solution may preferably be washed with an organic solvent such as toluene, ethyl acetate, or ether. The compound represented by the formula (6) wherein $A^1$ represents tert-butoxycarbonyl may be isolated by crystallization from the aqueous mixture obtained above or extraction with an organic solvent such as toluene, ethyl acetate, or ether. The compound represented by the formula (6) wherein $A^1$ represents tert-butoxycarbonyl may be obtained as optically active form without racemization from the optically active compound represented by the formula (13).

In the step II, cysteine or its salt is neutralized by alkali such as sodium hydroxide and reacted with methyl halide (normally more than 1.0 eq, preferably 1.0–1.1 eq), such as methyl iodide, in an aqueous solvent. An organic solvent such as THF, dioxane, or ether may be preferably used as a co-solvent. The reaction temperature between −10° and 50° C. is preferred and that between 0° and 30° C. is more preferred. The completion of the methylation reaction may be detected, for example, by TLC.

To the reaction mixture obtained above, di-tert-butyl dicarbonate (normally 1.0–1.5 eq) is added to react. The reaction may preferably be carried out under neutral or slight basic condition by addition of a base such as triethylamine, N-methylmorpholine, sodium hydroxide, or potassium hydroxide. The presence of a polar organic solvent such as THF or dioxane is also preferred. The reaction temperature between −10° and 50° C. is preferred and that between 0° and 30° C. is more preferred.

Acidification of the above reaction mixture gives the compound represented by the formula (5) wherein X represents methylthiomethyl and $A^3$ represents tert-butoxycarbonyl. As the acid for said acidification, a water soluble organic acid such as citric acid or mineral acid such as hydrochloric acid may be used and hydrochloric acid is cheap and more preferable. Before the acidification, the organic solvent used may preferably be distilled off and the resultant aqueous solution may preferably be washed with an organic solvent such as toluene, ethyl acetate, or ether. The compound represented by the formula (5), wherein X represents methylthiomethyl and $A^3$ represents tert-butoxycarbonyl, may be isolated by crystallization from the aqueous mixture obtained above or extraction with an organic solvent such as toluene, ethyl acetate, or ether. Said extract may be preferably washed with a solution of a reducing agent such as sodium bisulfite or sodium thiosulfate. The compound represented by the formula (5), wherein X represents methylthiomethyl and $A^3$ represents tert-butoxycarbonyl, may be obtained in an optically active form without racemization from optically active cysteine.

The present invention will be illustrated in more detail with reference to the following examples, which should not be construed to be limiting to the scope of the invention.

EXAMPLE 1

To a solution of 20.00 g (114 mmol) of L-cysteine hydrochloride monohydrate in 60 ml of water, 12 ml (1.4 eq) of 37% formalin containing 8% methanol was added and the resultant mixture was stirred for 6 h at room temperature. To this, 76 ml (2.0 eq) of 3N NaOH aqueous solution and a solution of 27.4 g (1.1 eq) of di-tert-butyl dicarbonate in 60 ml of THF were added and the mixture was stirred for 2 h. After addition of 8 ml (0.2 eq) of 3N NaOH aqueous solution, the reaction mixture was stirred overnight at room temperature, concentrated to remove THF under reduced pressure, washed with 80 ml of toluene, acidified by 23 ml of 6N hydrochloric acid, and extracted with 160 ml of ethyl acetate. The organic extract was concentrated under reduced pressure, dried by toluene azeotrope, and crystallized in hexane to give 25.37 g (Y. 95.3%) of (R)-3-tert-butoxycarbonyl-1,3-thiazolidine-4-carboxylic acid [Boc—Thz—OH].

$^1$H NMR (CDCl$_3$): δ 1.48 (s, 9H), 3.31 (bs, 2H), 4.3–4.9 (m, 3H), 8.27 (b, 1H).

EXAMPLE 2

To a solution of 125.0 g (712 mmol) of L-cysteine hydrochloride monohydrate in 250 ml of water, 475 ml (2.0 eq) of 3N NaOH aqueous solution and a solution of 106.1 g (1.05 eq) of iodomethane in 250 ml of THF were added successively under ice cooling. After stirring for 2 h at that temperature, 250 ml (1.05 eq) of 3N NaOH aqueous solution and a solution of 170.9 g ( 1.1 eq) of di-tert-butyl dicarbonate in 250 ml of THF were added and the mixture was stirred for 3.5 h at room temperature. After addition of 48 ml (0.2 eq) of 3N NaOH aqueous solution, the resultant mixture was stirred for 15 h at room temperature, concentrated to remove THF under reduced pressure, washed with 500 ml of toluene, acidified by 140 ml of 6N hydrochloric acid, and extracted with 1000 ml of ethyl acetate. The organic extract was washed with 500 ml of 5% NaCl aqueous solution containing 0.5% NaHSO$_3$, concentrated under reduced pressure, dried by toluene azeotrope, and crystallized in hexane to give 159.7 g (Y. 95%) of (R)-2-(N-tert-butoxycarbonylamino)-3-methylthiopropanoic acid [Boc—Mta—OH].

$^1$H NMR (CDCl$_3$): δ 1.46 (s, 9H), 2.16 (s, 3H), 2.99 (m, 2H), 4.55 (m, 1H), 5.39 (m, 1H), 8.79 (b, 1H).

EXAMPLE 3

Process 1

To a solution of 25.0 g (107 mmol) of (R)-3-tert-butoxycarbonyl-1,3-thiazolidine-4-carboxylic acid [Boc—Thz—OH: (R) configuration unless otherwise noted] in 200 ml of THF, 12.3 g (107 mmol) of N-hydroxysuccinimide [HOSu] and 24.3 g (118 mmol) of N,N'-dicyclohexylcarbodiimide [DCC] were added successively under ice cooling. After stirring for 1 h, 56.2 ml (535 mmol) of tert-butylamine was added under ice cooling and the reaction mixture was stirred for 1 h and filtered. The precipitates were washed with 200 ml of THF and the combined THF solution was concentrated under reduced pressure. The residue was dissolved in 200 ml of ethyl acetate, washed with 5% citric acid aqueous solution, and filtered. The organic solution was washed with 5% citric acid aqueous solution, 5% NaHCO$_3$ aqueous solution, and saturated NaCl aqueous solution successively, dried over Na$_2$SO$_4$, and concentrated under reduced pressure. The residue was crystallized by addition of 400 ml of hexane to give 22.8 g (Y. 74%) of Boc—Thz—NH-tBu.

$^1$H NMR (CDCl$_3$, 270 MHz): δ 1.35 (s, 9H), 1.49 (s, 9H), 3.20 (b, 1H), 3.36 (b, 1H), 4.35 (bd, 1H), 4.53 (b, 1H), 4.65 (d, 9.2 Hz, 1H), 5.96 (b, 1H).

HPLC: 19.5 min (column: YMC AM-302, 4.6×150; eluting solution A: 0.1% trifluoroacetic acid aqueous solution; eluting solution B: acetonitrile; linear gradient: 100% A to 100% B for 30 min; flow rate: 1.0 ml/min).

Process 2

To 6.49 g (22.5 mmol) of Boc—Thz—NH-tBu, 8.45 ml (67.6 mmol) of 8M solution of methanesulfonic acid in acetonitrile was added under ice cooling. After stirring for 5 min under ice cooling and for 40 min at room temperature, 70 ml of dichloromethane and 100 ml of 1N NaOH aqueous solution were added under ice cooling to extract the product. The resultant dichloromethane solution was washed with water, dried over Na$_2$SO$_4$, and concentrated under reduced pressure. The residue was crystallized by addition of 50 ml of hexane to give 3.50 g (Y. 83%) of H-Thz-NH-tBu.

$^1$H NMR (CDCl$_3$, 270 MHz): δ 1.35 (s, 9H), 2.37 (b, 1H), 3.08 (dd, 10.8 Hz, 7.6 Hz, 1H), 3.43 (dd, 10.8 Hz, 4.6 Hz, 1H), 3.95 (d, 9.8 Hz, 1H), 4.0 (m, 1H), 4.22 (d, 9.8 Hz, 1H), 6.88 (b, 1H).

HPLC: 10.1 min (condition: see process 1).

Process 3

To a solution of 3.22 g (10.9 mmol) of (2S,3S)-3-N-tert-butoxycarbonylamino-2-hydroxy-4-phenylbutanoic acid [Boc—AHPBA—OH: (2S,3S) configuration unless otherwise noted] and 2.26 g (12.0 mmol) of H-Thz-NH-tBu in 30 ml of DMF, 1.48 g (9.7 mmol) of 1-hydroxybenzotriazol [HOBt] monohydrate and 2.70 g (13.1 mmol) of DCC were added successively under ice cooling. The reaction mixture was stirred at room temperature overnight, filtered to remove N,N'-dicyclohexylurea, and concentrated under reduced pressure. To the residue, 50 ml of ethyl acetate and 50 ml of 5% NaHCO$_3$ aqueous solution were added and the resultant mixture was stirred for 3 h and filtered. The organic layer was washed with 5% NaHCO$_3$ aqueous solution, 5% citric acid aqueous solution, and saturated NaCl aqueous solution successively, dried over Na$_2$SO$_4$, and concentrated under reduced pressure. The residue was purified by silica-gel column chromatography (chloroform-methanol) to give 5.07 g (Y. 100%) of Boc-AHPBA-Thz-NH-tBu.

HPLC: 21.8 min (condition: see process 1).

Process 4

To 5.07 g (10.9 mmol) of Boc-AHPBA-Thz-NH-tBu, 27.3 ml (109 mmol) of 4M HCl solution in dioxane was added under ice cooling, and the reaction mixture was stirred for 2 h, concentrated under reduced pressure, and dissolved in 50 ml of DMF. To this, 1.52 ml (10.9 mmol) of triethylamine, 2.56 g (10.9 mmol) of (R)-2-N-tert-butoxycarbonylamino-3-methylthiopropanoic acid [Boc—Mta—OH: (R) configuration unless otherwise noted], 1.67 g (10.9 mmol) of HOBt monohydrate and 2.47 g (12.0 mmol) of DCC were added successively under ice cooling. The reaction mixture was stirred at room temperature overnight, filtered to remove N,N'-dicyclohexylurea, and concentrated under reduced pressure. To the residue, 100 ml of 5% citric acid aqueous solution was added and precipitates formed were collected by filtration. The precipitates were washed with 5% citric acid aqueous solution, 5% NaHCO$_3$ aqueous solution, and water successively, dried under reduced pressure, dissolved in 200 ml of hot THF, and filtered. The filtrate was concentrated under reduced pressure and residue was crystallized by addition of ether to give 5.15 g (Y. 81%) of Boc-Mta-AHPBA-Thz-NH-tBu.

HPLC: 22.0 min (condition: see process 1).

Process 5

To 2.00 g (3.44 mmol) of Boc-Mta-AHPBA-Thz-NH-tBu, 17.2 ml (68.7 mmol) of 4M HCl solution in dioxane was added under ice cooling, and the reaction mixture was stirred for 2 h, concentrated under reduced pressure, and dissolved in 20 ml of DMF. To this, 0.48 ml (3.44 mmol) of triethylamine, 0.91 g (4.47 mmol) of 5-isoquinolyloxyacetic acid [Qoa—OH], 0.53 g (3.44 mmol) of HOBt monohydrate and 0.92 g (4.47 mmol) of DCC were added successively under ice cooling. The reaction mixture was stirred at room temperature overnight, filtered to remove N,N'-dicyclohexylurea, and concentrated under reduced pressure. To the residue, 100 ml of 5% NaHCO$_3$ aqueous solution was added and extracted with 100 ml of ethyl acetate. The organic layer was washed with 5% NaHCO$_3$ aqueous solution and saturated NaCl aqueous solution successively, dried under dried over Na$_2$SO$_4$, and concentrated under reduced pressure. The residue was crystallized by addition of hexane to give 2.24 g (Y. 95%) of Qoa-Mta-AHPBA-Thz-NH-tBu.

HPLC: 14.0 min (column: YMC AM-302, 4.6×150; eluting solution A: 0.1% trifluoroacetic acid aqueous solution; eluting solution B: acetonitrile; linear gradient: 20% B to 80% B for 30 min; flow rate: 0.7 ml/min).

Process 6

To a solution of 101 mg (147 mmol) of Qoa-Mta-AHPBA-Thz-NH-tBu in 700 ml of ethanol, 300 ml (150 mmol) of 0.5M solution of acetic acid in ethanol was added.

After standing at room temperature for 3 days, the corresponding acetate salt was obtained by centrifugation.

EXAMPLE 4

To a solution of 5.0 g (21.4 mmol) of Boc—Thz—OH in 30 ml of THF, 3.28 g (21.4 mmol) of HOBt monohydrate and 4.86 g (23.6 mmol) of DCC were added successively under ice cooling. After stirring for 1.5 h, a solution of 6.8 ml (65 mmol) of tert-butylamine in 20 ml of THF was added under ice cooling and the reaction mixture was stirred for 2 h and filtered. To the filtrate, 50 ml of toluene and 50 ml of 5% citric acid aqueous solution were added, and the resultant mixture was stirred and filtered. The organic layer was washed with 5% citric acid aqueous solution, 5% NaHCO$_3$ aqueous solution, and saturated NaCl aqueous solution successively, dried over Na$_2$SO$_4$, and concentrated under reduced pressure. The residue was crystallized by addition of 100 ml of hexane to give 4.92 g (Y. 80%) of Boc—Thz—NH-tBu which was convened to Qoa-Mta-AHPBA-Thz-NH-tBu by a similar method the processes 2–5 of the Example 3.

EXAMPLE 5

To a solution of 3.0 g (12.9 mmol) of Boc-Thz-OH and 2.15 ml (15.5 mmol) of triethylamine in 25 ml of DMF, 2.02 ml (15.5 mmol) of isobutyl chloroformate was added dropwise at −15° C. After stirring for 10 min at that temperature. 4.06 ml (38.7 mmol) of tert-butylamine was added. The reaction mixture was stirred for 10 min at that temperature and 100 min under ice cooling, concentrated under reduced pressure, diluted with 50 ml of ethyl acetate, washed with 5% NaHCO$_3$ aqueous solution, 5% citric acid aqueous solution, and saturated NaCl aqueous solution successively, dried over Na$_2$SO$_4$, and evaporated under reduced pressure to give 3.13 g (Y. 84%) of Boc-Thz-NH-tBu which was convened to Qoa-Mta-AHPBA-Thz-NH-tBu by a similar method with processes 2–5 of Example 3.

EXAMPLE 6

To a solution of 3.0 g (12.9 mmol) of Boc—Thz—OH and 1.97 ml (14.2 mmol) of triethylamine in 30 ml of DMF, 1.75 ml (14.2 mmol) of pivaloyl chloride was added dropwise at −20° C. After stirring for 15 min at that temperature, 4.06 ml (38.7 mmol) of tert-butylamine was added. The reaction mixture was allowed to warm to room temperature during 4 h with stirring. A similar work-up with that of Example 5 gave 3.53 g (Y. 95%) of Boc—Thz-NH-tBu which was convened to Qoa-Mta-AHPBA-Thz-NH-tBu by a similar method with processes 2–5 of Example 3.

EXAMPLE 7

To 3.25 g (11.3 mmol) of Boc-Thz-NH-tBu, 15 ml (195 mmol) of trifluoroacetic acid was added under ice cooling and the resultant mixture was stirred at that temperature for 30 min and evaporated. The residue was washed with hexane by decantation and partitioned between chloroform and 1N NaOH aqueous solution. The organic layer was dried over Na$_2$SO$_4$ and evaporated under reduced pressure to give 2.00 g (Y. 94%) of H-Thz-NH-tBu which was convened to Qoa—Mta—AHPBA—Thz—NH-tBu by a similar method with processes 3–5 of Example 3.

EXAMPLE 8

To a solution of 5.00 g (17.4 mmol) of Boc-Thz-NH-tBu in 23.7 ml of acetonitrile-dichloromethane (1:6), 3.39 ml (52.1 mmol) of methanesulfonic acid was added. After stirring at room temperature for 1.5 h, 30 ml of dichloromethane and 26 ml (52 mmol) of 2N NaOH aqueous solution were added under ice cooling to extract the product. The organic layer was washed with 5% NaHCO$_3$ aqueous solution and saturated NaCl aqueous solution successively, dried over Na$_2$SO$_4$, and evaporated under reduced pressure. The residue was triturated in 50 ml of hexane to give 2.86 g (Y. 88%) of H-Thz-NH-tBu which was converted to Qoa-Mta-AHPBA-Thz-NH-tBu by a similar method with processes 3–5 of Example 3.

EXAMPLE 9

To 1.96 g (6.8 mmol) of Boc-Thz-NH-tBu, 17 ml (68 mmol) of 4M HCl solution in dioxane was added under ice cooling. After stirring for 30 min, the reaction mixture was concentrated under reduced pressure and the residue was dissolved in 60 ml of DMF. To the resultant solution, 0.95 ml (6.8 mmol) of triethylamine, 1.80 g (6.8 mmol) of Boc-AHPBA-OH, 100 g (7.5 mmol) of HOBt monohydrate, and 1.56 g (8.2 mmol) of 1-ethyl-3-(3-N,N-dimethylaminopropyl) carbodiimide [EDC] hydrochloride were added successively under ice cooling. The reaction mixture was allowed to warm to room temperature and stirred overnight, and concentrated under reduced pressure. The residue was dissolved in ethyl acetate, washed with 5% citric acid aqueous solution, 5% NaHCO$_3$ aqueous solution, and saturated NaCl aqueous solution successively, dried over Na$_2$SO$_4$, and evaporated under reduced pressure to give 2.69 g (Y. 87%) of Boc—AHPBA-Thz-NH-tBu which was converted to Qoa—Mta—AHPBA-Thz-NH-tBu by a similar method with a processes 4–5 of the Example 3.

EXAMPLE 10

Process 1

To 2.00 g (4.3 mmol) of Boc-AHPBA-Thz-NH-tBu, 4.30 ml (17.2 mmol) of 4M methanesulfonic acid solution in chloroform-acetonitrile (1:1) was added under ice cooling. After stirring for 30 min, the reaction mixture was diluted with 10 ml of DMF. To the resultant solution, 2.51 ml (18 mmol) of triethylamine, 1.01 g (4.30 mmol) of Boc-Mta-OH, 0.658 g (4.30 mmol) of HOBt monohydrate, and 0.907 g (4.73 mmol) of EDC hydrochloride were added successively under ice cooling. The reaction mixture was stirred at room temperature overnight and diluted with 5% NaHCO$_3$ aqueous solution. The precipitates formed were collected by filtration and washed with water. A subsequent re-precipitation from DMF-DMSO-water gave 1.90 g (Y. 76%) of Boc-Mta-AHPBA-Thz-NH-tBu.

Process 2

To a suspension of 100 mg (0.17 mmol) of Boc-Mta-AHPBA-Thz-NH-tBu in 0.2 ml of acetonitrile-dichloromethane (1:1), 67 μl (1.03 mmol) of methanesulfonic acid was added. After stirring for 30 min, the reaction mixture was diluted with 0.3 ml of DMF. To the resultant mixture, 14.3 μl (1.03 mmol) of triethylamine, 35 mg (0.17 mmol) of Qoa—OH, 23 mg (0.17 mmol) of HOBt monohydrate, and 40 mg (0.21 mmol) of EDC hydrochloride were added successively under ice cooling. The reaction mixture was stirred at room temperature overnight, diluted with 5% NaHCO$_3$ aqueous solution, and extracted with ethyl acetate. The organic layer was evaporated under reduced pressure and the residue was crystallize by addition of hexane to give 94 mg (Y. 80%) of Qoa—Mta—AHPBA—Thz—NH-tBu.

EXAMPLE 11

Process 1

To a solution of 20.0 g (85.1 mmol) of Boc—Mta—OH, 9.79 g (85.1 mmol) of HOSu, and 0.67 ml (8.5 mmol) of pyridine in 100 ml of THF, 21.0 g (102 mmol) of DCC was added under ice cooling. After stirring at room temperature for 15 h, the reaction mixture was filtered to remove N,N'-dicyclohexylurea, and concentrated under reduced pressure. To the residue, 200 ml of 2-propanol was added to crystallize 17.6 g (Y. 62%) of Boc—Mta—OSu.

$^1$H NMR (CDCl$_3$, 270 MHz): δ 1.47 (s, 9H), 2.19 (s, 3H), 2.85 (s, 4H), 3.02 (ABX, 14.2 Hz, 6.2 Hz, 1H), 3.12 (ABX, 14.2 Hz, 5.1 Hz, 1H), 4.88 (m, 1H), 5.34 (m, 1H).

Process 2

To 8.64 g (18.6 mmol) of Boc-AHPBA-Thz-NH-tBu, 46.5 ml (186 mmol) of 4M HCl solution in dioxane was added, and the reaction mixture was stirred for 1.5 h, concentrated under reduced pressure, and dissolved in 50 ml of DMF. To this, 2.58 ml (18.6 mmol) of triethylamine and 7.40 g (22.3 mmol) of Boc-Mta-OSu were added successively under ice cooling. After stirring for 1.5 h, 0.83 ml (5.9 mmol) of triethylamine was added and stirring was continued for 1.5 h. The reaction mixture was filtered and the filtrate was concentrated under reduced pressure. To the residue, 200 ml of 5% NaHCO$_3$ aqueous solution and 20 ml of ether were added and precipitates formed were collected by filtration. The precipitates were washed with 5% NaHCO$_3$ aqueous solution, 5% citric acid aqueous solution, water, 50% aqueous acetone, and hexane successively, dried under reduced pressure to give 9.00 g (Y. 83%) of Boc-Mta-AHPBA-Thz-NH-tBu which was converted to Qoa-Mta-AHPBA-Thz-NH-tBu by the similar method with the process 5 of the Example 3.

EXAMPLE 12

To a solution of 3.00 g (12.8 mmol) of Boc—Mta—OH and 1.78 g (12.8 mmol) of p-nitrophenol [HONp] in 16 ml of THF-chloroform (1:1), 2.89 g (14.1 mmol) of DCC was added under ice cooling. After stirring for 1h, the reaction mixture was filtered to remove N,N'-dicyclohexylurea, and concentrated under reduced pressure.

To the residue, 2-propanol is added to crystallize Boc—Mta—ONp which is used in stead of Boc-Mta-OSu in the similar method with the process 2 of the Example 11 and converted to Qoa-Mta-AHPBA-Thz-NH-tBu.

EXAMPLE 13

To 1.50 g (2.58 mmol) of Boc—Mta—AHPBA—Thz—NH-tBu, 13 ml (52 mmol) of 4M HCl solution in dioxane was added under ice cooling, and the reaction mixture was stirred for 80 min, concentrated under reduced pressure, and dissolved in 15 ml of DMF. To this, 0.36 ml (2.58 mmol) of triethylamine, 0.57 g (2.84 mmol) of 1-naphthoxyacetic acid [Noa-OH], 0.40 g (2.58 mmol) of HOBt monohydrate and 0.58 g (2.83 mmol) of DCC were added successively under ice cooling. The reaction mixture was stirred at room temperature overnight and treated similarly with the process 5 of the Example 3 to give 1.40 g (Y. 81%) of Noa-Mta-AHPBA-Thz-NH-tBu.

EXAMPLE 14

Process 1

To a solution of 5.00 g (19.1 mmol) of (R)-3-tert-butoxycarbonyl-5,5-dimethyl-1,3-thiazolidine-4-carboxylic acid [Boc-Dtc-OH: (R) configuration unless otherwise noted] in 40 ml of THF, 2.20 g (19.1 mmol) of HOSu and 4.30 g (21.0 mmol) of DCC were added successively under ice cooling. After stirring for 2 h at room temperature, 10 ml (21 mmol) of tert-butylamine was added under ice cooling and the reaction mixture was treated similarly with the process 1 of the Example 3 to give 4.20 g (Y. 70%) of Boc-Dtc-NH-tBu.

$^1$H NMR (CDCl$_3$, 270 MHz): δ 1.35 (s, 9H), 1.42 (s, 3H), 1.46 (s, 9H), 1.55 (s, 3H), 3.90 (bs, 1H), 4.62 (s, 2H), 5.76 (b, 1H).

Process 2

To 15.0 g (47.4 mmol) of Boc—Dtc—NH-tBu, 17.6 ml (141 mmol) of 8M solution of methanesulfonic acid in acetonitrile was added. After stirring for 1 h, 90 ml of ether and 49 ml of 4N NaOH aqueous solution were added under ice cooling to extract the product. The aqueous layer was extracted with 100 ml of ether and the combined ether solution was washed with 5% NaHCO$_3$ aqueous solution and saturated NaCl aqueous solution successively, dried over Na$_2$SO$_4$, and evaporated under reduced pressure. The residue was crystallized by addition of 15 ml of hexane to give 9.9 g (Y. 97%) of H-Dtc-NH-tBu.

$^1$H NMR (CDCl$_3$, 270 MHz): δ 1.32 (s, 3H), 1.37 (s, 9H), 1.68 (s, 3H), 2.8 (b, 1H), 3.32 (s, 1H), 4.17 and 4.26 (AB, 9.7 Hz, 2H), 6.31 (b, 1H).

Process 3

To a solution of 4.09 g (13.8 mmol) of Boc—AHPBA—OH and 3.00 g (13.8 mmol) of H—Dtc—NH-tBu in 15 ml of DMF-chloroform (1:1), 2.12 g (13.8 mmol) of HOBt monohydrate and 3.14 g (15.2 mmol) of DCC were added successively under ice cooling. The reaction mixture was stirred at room temperature for 2 days and concentrated under reduced pressure. To the residue, 40 ml of ether and 40 ml of 5% citric acid aqueous solution were added and the resultant mixture was stirred for 15 min and filtered. The organic layer was washed with 5% citric acid aqueous solution, filtered, washed with 5% NaHCO$_3$ aqueous solution and saturated NaCl aqueous solution successively, dried over Na$_2$SO$_4$, and evaporated under reduced pressure to give 6.38 g (Y. 93%) of Boc-AHPBA-Dtc-NH-tBu.

Process 4

To 3.00 g (6.07 mmol) of Boc—AHPBA—Dtc—NH-tBu, 15.2 ml (60.8 mmol) of 4M HCl solution in dioxane was added under ice cooling, and the reaction mixture was stirred for 1 h, concentrated under reduced pressure, and dissolved in 15 ml of DMF-chloroform (1:1). To this, 0.845 ml (6.07 mmol) of triethylamine, 1.43 g (6.08 mmol) of Boc—Mta—OH, 0.93 g (6.07 mmol) of HOBt monohydrate and 1.38 g (6.7 mmol) of DCC were added successively under ice cooling. The reaction mixture was allowed to warm to room temperature, stirred overnight, and concentrated under reduced pressure. To the residue, 40 ml of ether and 40 ml of 5% citric acid aqueous solution were added and the resultant mixture was stirred for 15 min and filtered. The organic layer was washed with 5% citric acid aqueous solution, filtered, washed with 5% NaHCO$_3$ aqueous solution and saturated NaCl aqueous solution successively, dried over Na$_2$SO$_4$, and evaporated under reduced pressure to give 3.43 g (Y. 92%) of Boc-Mta-AHPBA-Dtc-NH-tBu.

Process 5

To 1.90 g (3.11 mmol) of Boc-Mta-AHPBA-Dtc-NH-tBu, 7.7 ml (31 mmol) of 4M HCl solution in dioxane was added under ice cooling, and the reaction mixture was stirred for 1 h, concentrated under reduced pressure, and dissolved in 15 ml of DMF. To this, 0.475 ml (3.4 mmol) of triethylamine, 0.82 g (4.0 mmol) of 5Qoa—OH, 0.48 g (3.11 mmol) of HOBt monohydrate and 0.83 g (4.0 mmol) of DCC were added successively under ice cooling. The reaction mixture was allowed to warm to room temperature, stirred overnight, and concentrated under reduced pressure. To the residue, 40 ml of ethyl acetate and 40 ml of 5% NaHCO$_3$ aqueous solution were added and the resultant mixture was stirred for 15 min and filtered. The organic layer was washed with 5% NaHCO$_3$ aqueous solution and saturated NaCl aqueous solution successively, dried over Na$_2$SO$_4$, and evaporated under reduced pressure. The residue was crystallized from ethyl acetate-hexane to give 1.60 g (Y. 74%) of Qoa—Mta—AHPBA—Dtc—NH-tBu.

EXAMPLE 15

To a solution of 5.15 g (34.5 mmol) of L-penicillamine in 50 ml of water, 3.4 ml (1.3 eq) of 37% formalin containing 8% methanol was added and the resultant mixture was stirred overnight at room temperature. To this, 7.2 ml (1.5 eq) of triethylamine and a solution of 9.07 g (1.2 eq) of di-tert-butyl dicarbonate in 50 ml of THF were added and the mixture was stirred for 8 h at room temperature, washed with ether, acidified (pH 3) by citric acid, and extracted with ethyl acetate. The organic extract was washed with 5% citric acid aqueous solution and saturated NaCl aqueous solution successively, dried over Na$_2$SO$_4$, evaporated under reduced pressure, and crystallized in hexane to give 8.39 g (Y. 92%) of (R)-3-tert-butoxycarbonyl-5,5-dimethyl-1,3-thiazolidine-4-carboxylic acid [Boc—Dtc—OH].

$^1$H NMR (CDCl$_3$): δ 1.44 (s, 3H), 1.49 (s, 9H), 1.61 (s, 3H), 4.22 and 4.35 (b, 1H), 4.63 and 4.69 (b, 2H), 7.7 (b, 1H)

EXAMPLE 16

Process 1

To a solution of 3.48 g (11.8 mmol) of Boc—AHPBA—OH and 2.55 g (11.8 mmol) of H—Dtc-NH-tBu in 13 ml of DMF-dichloromethane (1:1), 1.81 g (11.8 mmol) of HOBt monohydrate and 2.43 g (11.8 mmol) of DDC were added successively under ice cooling. The reaction mixture was stirred for 20 h at room temperature and concentrated under reduced pressure. To the residue, 30 ml of ether and 30 ml of 5% citric acid aqueous solution were added and the resultant mixture was stirred and filtered. The organic layer was washed with 5% citric acid aqueous solution, filtered, washed with 5% NaHCO$_3$ aqueous solution and saturated NaCl aqueous solution successively, dried over Na$_2$SO$_4$, and evaporated under reduced pressure to give 5.02 g (Y. 89%) of Boc-AHPBA-Dtc-NH-tBu.

Process 2

To 3.95 g (8.0 mmol) of Boc—AHPBA—Dtc—NH-tBu, 20 ml (80 mmol) of 4M HCl solution in dioxane was added, and the reaction mixture was stirred for 30 min at room temperature, concentrated under reduced pressure, and dissolved in 50 ml of DMF. To this, 1.1 ml (8.0 mmol) of triethylamine, 4.24 g (12.0 mmol) of p-nitrophenyl (S)-2-tert-butoxycarbonylamino-3-carbamoylpropanoate [Boc—Asn—ONp: (S) configuration unless otherwise noted], and 1.3 ml (12.0 mmol) of N-methylmorpholine were added successively under ice cooling. After stirring for 1 h at room temperature, 1.84 g (12.0 mmol) of HOBt monohydrate was added and stirring was continued for 14 h. The reaction mixture was concentrated under reduced pressure and partitioned between 100 ml of ethyl acetate and 50 ml of 5% NaHCO₃ aqueous solution. The aqueous layer was extracted with 50 ml of ethyl acetate and the combined organic solution was washed with 5% NaHCO₃ aqueous solution, 5% citric acid aqueous solution, and saturated NaCl aqueous solution successively, dried over Na₂SO₄, evaporated under reduced pressure to give 5.20 g of crude Boc-Asn-AHPBA-Dtc-NH-tBu. To 2.60 g of the crude product, 10 ml (40 mmol) of 4M HCl solution in dioxane was added, and the mixture was stirred for 1 h at room temperature, and evaporated under reduced pressure. The residue was triturated in ether to give 1.76 g (Y. 81%) of H-Asn-AHPBA-Dtc-NH-tBu hydrochloride.

Process 3

To a solution of 1.45 g (2.7 mmol) of H-Asn-AHPBA-Dtc-NH-tBu hydrochloride in 20 ml of DMF, 0.37 ml (2.7 mmol) of triethylamine, 0.59 g (2.9 mmol) of 1-naphthoxyacetic acid [Noa—OH], 0.41 g (2.7 mmol) of HOBt monohydrate and 0.60 g (2.9 mmol) of DCC were added successively under ice cooling. The reaction mixture was stirred at room temperature overnight, filtered to remove insoluble matter, and partitioned between 50 ml of ethyl acetate and 20 ml of 5% citric acid aqueous solution. The aqueous layer was extracted with 30 ml of ethyl acetate and the combined organic solution was washed with 5% citric acid aqueous solution, 5% NaHCO₃ aqueous solution, and saturated NaCl aqueous solution successively, dried over Na₂SO₄, evaporated under reduced pressure, and purified by silica-gel column chromatography (chloroform-methanol) to give 1.10 g (Y. 59%) of Noa—Asn—AHPBA—Dtc—NH-tBu.

EXAMPLE 17

Process 1

To a suspension of 2.03 g (10 mmol) of Qoa—OH and 1.35 g (10 mmol) of HOBt in 10 ml of DMF, a solution of 2.27 g (11 mmol) of DCC in 10 ml of DMF was added under ice cooling and the resultant mixture was stirred for 1 h. To this, a DMF solution of (R)-methylthioalanine methyl ester [H—Mta—OCH₃], which was prepared from 1.86 g (10 mmol) of the corresponding hydrochloride by neutralization with 1.39 ml (10 mmol) of triethylamine in 15 ml of DMF, was added under ice cooling and the reaction mixture was allowed to warm to room temperature, stirred overnight, and diluted with 50 ml of ethyl acetate. To this, 70 ml of 10% citric acid aqueous solution was added dropwise under ice cooling and the mixture was stirred for 20 min at room temperature and filtered. To the filtrate, 50 ml of 10% NaHCO₃ aqueous solution was added and the aqueous layer was extracted with ethyl acetate. The combined organic solution was washed with 5% NaHCO₃ aqueous solution and 5% NaCl aqueous solution successively, treated with 0.2 g of activated carbon, and evaporated under reduced pressure. The residue was crystallized by addition of hexane to give 2.28 g (Y. 68%) of Qoa—Mta—OCH₃.

Process 2

To a solution of 1.34 g (4.0 mmol) of Qoa—Mta—OCH₃ in 20 ml of methanol, 1.0 ml (4.0 mmol) of 4N NaOH aqueous solution was added under ice cooling. After stirring for 3.5 h, the reaction mixture was neutralized by 0.23 ml (4.0 mmol) of acetic acid and evaporated under reduced pressure. The residue was dissolved in 40 ml of 0.1N NaOH aqueous solution, filtered to remove insoluble matter, and washed with 20 ml of dichloromethane. The aqueous solution was neutralized with 1N hydrochloric acid to adjust pH 7 and the precipitates formed were collected by filtration, washed with 10 ml of cold water, and dried under reduced pressure to give 0.89 g (Y. 70%) of Qoa-Mta-OH.

Process 3

To a solution of 15.8 g (34 mmol) of Boc-AHPBA-Thz-NH-tBu, which was prepared by the similar method with the process 1–3 of the Example 3, in 40 ml of dichloromethane, 85 ml (340 mmol) of 4M HCl solution in dioxane was added. After stirring for 2 h, the reaction mixture was diluted with 240 ml of water and filtered. The aqueous layer of the filtrate was diluted with 80 ml of methanol, neutralized by portionwise addition of 34 g of NaHCO₃, and stirred overnight. The precipitates formed were collected by filtration, washed with 80 ml of water-methanol (1:1), and dried under reduced pressure to give 8.12 g (Y. 65%) of H—AHPBA-Thz-NH-tBu.

Process 4

To a solution of 1.31 g (4.1 mmol) of Qoa—Mta—OH, 1.50 g (4.1 mmol) of H—AHPBA—Thz-NH-tBu, and 0.55 g (4.1 mmol) of HOBt in 38 ml of DMF, a solution of 0.93 g (4.5 mmol) of DCC in 3 ml of DMF was added under ice cooling and the reaction mixture was allowed to warm to room temperature, stirred overnight, and diluted with 30 ml of ethyl acetate. To this, 30 ml of 10% citric acid aqueous solution was added dropwise under ice cooling and the mixture was stirred for 1 h at room temperature and filtered. To the filtrate, 20 ml of 5% NaHCO₃ aqueous solution was added and the aqueous layer was extracted with 30 ml of ethyl acetate. The combined organic solution was washed with 5% K₂CO₃ aqueous solution and 5% NaCl aqueous solution successively, and evaporated under reduced pressure. The residue was purified by silica-gel column chromatography (dichloromethane-ethanol) to give 2.30 g (Y. 84%) of Qoa-Mta-AHPBA-Thz-NH-tBu.

EXAMPLE 18

Process 1

To a solution of 1.00 g (2.74 mmol) of H—AHPBA—Thz—NH-tBu, 0.60 g (2.74 mmol) of Boc—Val—OH, and 0.37 g (2.74 mmol) of HOBt in 15 ml of DMF, 0.58 g (3.01 mmol) of EDC hydrochloride was added under ice cooling. After stirring overnight at room temperature, the reaction mixture was diluted with 90 ml of 5% citric acid aqueous solution. The precipitates formed were collected by filtration, washed with 3% K₂CO₃ aqueous solution and hot methanol successively, and dried under reduced pressure to give 0.92 g (Y. 60%) of Boc—Val—AHPBA-Thz-NH-tBu.

Process 2

To 0.92 g (1.64 mmol) of Boc-Val-AHPBA-Thz-NH-tBu, 4.1 ml (16 mmol) of 4M HCl solution in dioxane was added, and the reaction mixture was stirred for 1 h at room temperature, concentrated under reduced pressure, and diluted with ether. The precipitates formed were collected by filtration, dried under reduced pressure, and dissolved in 10 ml of DMF. To this, 0.23 ml (1.64 mmol) of triethylamine, 0.40 g (1.97 mmol) of Qoa—OH, 0.30 g (1.97 mmol) of HOBt, and 0.38 g (1.97 mmol) of EDC hydrochloride were added successively under ice cooling and the reaction mixture was stirred overnight at room temperature. After evaporation under reduced pressure, the residue was partitioned between ethyl acetate and 5% NaHCO₃ aqueous solution. The organic solution was washed with saturated NaCl aqueous solution, dried over Na₂SO₄, evaporated under reduced pressure, and purified by silica-gel column chromatography to give 0.65 g (Y. 60%) of Qoa-Val-AHPBA-Thz-NH-tBu.

EXAMPLE 19

The similar method with the process 2 of the Example 18 may give Pyoa-Val-AHPBA-Thz-NH-tBu by use of 3-pyridyloxyacetic acid [Pyoa-OH] instead of Qoa—OH.

EXAMPLE 20

To a solution of 0.43 g (3.19 mmol) of HOBt and 0.41 mL (2.95 mmol) of triethylamine in 15.0 mL of DMF, was added 0.61 mL (2.94 mmol) of diphenylphosphoryl chloride under ice cooling, and the reaction mixture was stirred for 3 h. To this were added 0.60 g (2.94 mmol) of Qoa—OH, 1.18 g (2.45 mmol) of H—Mta—AHPBA—Thz—NHtBu, and 0.75 mL (5.40 mmol) of triethylamine under ice-cooling and stirred at room temperature over night. Then 75 mL of dichloromethane and 75 mL of water were added to the reaction mixture, and the organic layer was washed with 3% Na₂CO₃ aqueous solution (75 mL×2) and 5% NaCl aqueous solution (75 mL×2) successively, dried over MgSO₄ and activated carbon, and concentrated under reduced pressure to give 1.56 g of the crude product. The crude product was recrystallized from 12.5 mL of ethanol to give 1.13 g (Y. 68.8%) of Qoa—Mta—AHPBA—Thz—NHtBu.

EXAMPLE 21

To a solution of 1.05 g (5.18 mmol) of Qoa—OH, 0.80 g (5.92 mmol) of HOBt, and 1.55 mL (11.1 mmol) of triethylamine in 12.5 mL of DMF, was added 1.13 mL (5.43 mmol) of diphenylphosphoryl chloride under ice cooling, and the reaction mixture was stirred for 3 h. To this was added a solution of 2.38 g (4.94 mmol) of H—Mta—AHPBA—Thz—NHtBu in 12.5 mL of dichloromethane under ice-cooling and stirred at room temperature over night. Then 50 mL of dichloromethane and 50 mL of water were added to the reaction mixture, and the organic layer was washed with 3% Na₂CO₃ aqueous solution (50 mL×3) and 5% NaCl aqueous solution (50 mL) successively, dried over MgSO₄, and concentrated under reduced pressure to give 3.31 g of the crude product. A part of the crude product (2.90 g) was recrystallized from 29 mL of acetone to give 2.49 g (Y. 86.3%) of Qoa—Mta—AHPBA—Thz—NHtBu.

EXAMPLE 22

To a solution of 1.07 g (5.25 mmol) of Qoa—OH, 1.08 g (6.00 mmol) of HONb, and 1.67 mL (12.0 mmol) of triethylamine in 12.5 mL of DMF, was added 1.14 mL (5.50 mmol) of diphenylphosphoryl chloride under ice cooling, and the reaction mixture was stirred for 3 h. To this was added a solution of 2.41 g (5.00 mmol) of H—Mta—AHPBA—Thz—NHtBu in 12.5 mL of dichloromethane under ice-cooling and stirred at room temperature over night. Then 50 mL of dichloromethane and 50 mL of water were added to the reaction mixture, and the organic layer was washed with 3% Na₂CO₃ aqueous solution (50 mL×3) and 5% NaCl aqueous solution (50 mL) successively, dried over MgSO₄, and concentrated under reduced pressure to give 3.32 g of the crude product. A part of the crude product (3.00 g) was recrystallized from 30 mL of acetone to give 2.72 g (Y. 90.3%) of Qoa—Mta—AHPBA—Thz—NHtBu.

What is claimed is:

1. A process for producing peptide derivatives represented by formula (1) and salts thereof:

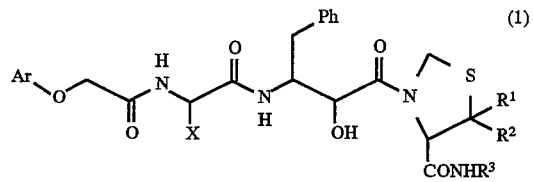

said process comprising Step E: a condensation reaction of an amino amide represented by formula (9):

with a protected amino acid represented by formula (10):

using a carbodiimide-additive method as a condensation method of said Step E which gives a protected peptide represented by formula (11):

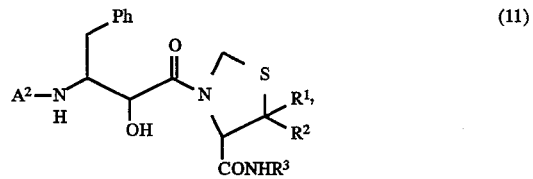

Step F: deprotection of said protected peptide of formula (11) which gives a peptide represented by formula (4):

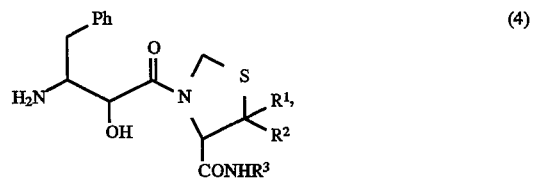

Step B: a condensation reaction of said peptide of formula (4) with a protected amino acid represented by formula (5):

which gives a protected peptide of formula (12):

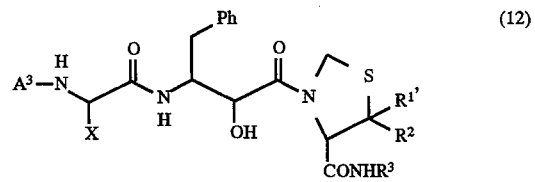

Step G: deprotection of said protected peptide of formula (12) which gives a peptide represented by formula (2):

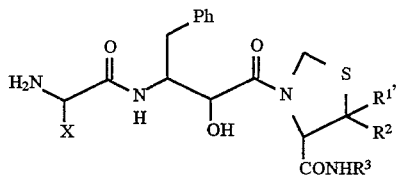 (2)

and Step A: a condensation reaction of said peptide of formula (2) with a carboxylic acid represented by formula (3):

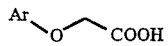 (3)

which gives said peptide derivative of formula (1); or a process comprising said Step E using a carbodiimide-additive method, said Step F, and Step B': a condensation reaction of said peptide of formula (4) with a N-acylated amino acid of formula (5'):

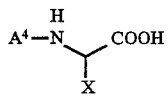 (5')

which also gives said peptide of formula (1) wherein $R^1$ and $R^2$ each represents a lower alkyl group or a hydrogen atom, $R^3$ represents a lower alkyl group, X represents methylthiomethyl, methanesulfonylmethyl, or carbamoylmethyl, Ar represents a 1-naphthyl group or 5-isoquinolyl group, $A^2$ and $A^3$ each represents an amino protective group, and $A^4$ represents an acyl group derived from the carboxylic acid represented by formula (3).

2. The process of claim 1, wherein the additive for said carbodiimide-additive method of said Step E is 1-hydroxybenzotriazole.

3. The process of claim 1, wherein said Step A comprises a reaction of said carboxylic acid of formula (3):

 (3)

with a hydroxyl compound represented by formula (17):

 (17)

which intermediately generates an activated ester represented by formula (14):

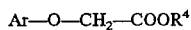 (14)

wherein Ar represents a 1-naphthyl group or 5-isoquinolyl group, and $R^4$ represents a compound selected from the group consisting of benzotriazol-1-yl, succinimido, 5-norbornene-2,3-dicarboximido and nitrophenyl.

4. The process of claim 5, wherein said reaction of the carboxylic acid of formula (3) with the hydroxyl compound of formula (17) is carried out using a carbodiimide.

5. A process for producing peptide derivatives represented by formula (1) and salts thereof:

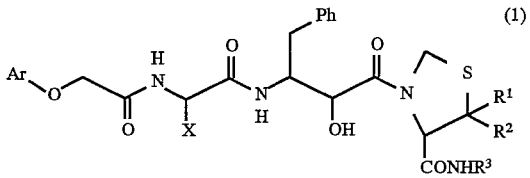 (1)

said process comprising Step A: a condensation of a peptide of formula (2):

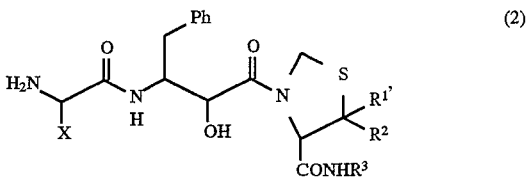 (2)

with a carboxylic acid represented by formula (3)

 (3)

wherein said step A comprises a reaction of said carboxylic acid of formula (3) with a hydroxyl compound represented by formula (17):

HO—R⁴ (17)

which intermediately generates an activated ester represented by formula (14):

Ar—O—CH₂—COOR⁴ (14)

wherein said reaction of the carboxylic acid of formula (3) with a hydroxyl compound of formula (17) is carried out using a phosphoryl chloride represented by formula (16):

$(R^5O)(R^6O)P(=O)Cl$ (16)

which gives said peptide derivative of formula (1), wherein $R^1$ and $R^2$ each represents a lower alkyl group or a hydrogen atom, $R^3$ represents a lower alkyl group, $R^4$ represents a compound selected from the group consisting of benzotriazol-1-yl, succinimido, 5-norbornene-2,3-dicarboximido and nitrophenyl, X represents methylthiomethyl, methanesulfonylmethyl, or carbamoylmethyl group, Ar represents an aryl group or heteroaryl group, and $R^5$ and $R^6$ each represents a hydrocarbon group having from 1 to 7 carbon atoms.

6. The process of claim 5, wherein said phosphoryl chloride of formula (16) is diphenylphosphoryl chloride.

7. The process of claim 5, wherein said hydroxyl compound of formula (17) is 1-hydroxybenzotriazole or N-hydroxy-5-norbornene-2,3-dicarboximide.

* * * * *